(12) United States Patent
Hodges, IV

(10) Patent No.: US 11,432,955 B2
(45) Date of Patent: *Sep. 6, 2022

(54) SYSTEMS AND METHODS FOR ORTHOPEDIC SUPPORTS

(71) Applicant: Therapeutic Envisions, Inc., Libertyville, IL (US)

(72) Inventor: Charles Edward Hodges, IV, Sumter, SC (US)

(73) Assignee: Therapeutic Envisions, Inc., Libertyville, IL (US)

( * ) Notice: Subject to any disclaimer, the term of this patent is extended or adjusted under 35 U.S.C. 154(b) by 387 days.

This patent is subject to a terminal disclaimer.

(21) Appl. No.: 16/287,703

(22) Filed: Feb. 27, 2019

(65) Prior Publication Data
US 2019/0192328 A1 Jun. 27, 2019

Related U.S. Application Data

(63) Continuation-in-part of application No. 15/242,139, filed on Aug. 19, 2016, now abandoned, and a
(Continued)

(51) Int. Cl.
*A61F 5/01* (2006.01)
*A61F 5/30* (2006.01)
(Continued)

(52) U.S. Cl.
CPC .......... *A61F 5/0123* (2013.01); *A61F 5/0104* (2013.01); *A61F 5/0106* (2013.01);
(Continued)

(58) Field of Classification Search
CPC .... A61F 5/0104; A61F 5/0106; A61F 5/0109; A61F 5/0118; A61F 5/0123;
(Continued)

(56) References Cited

U.S. PATENT DOCUMENTS 2,238,804 A 4/1941 Brown
3,318,305 A 5/1967 Schultz
(Continued)

*Primary Examiner* — Keri J Nelson
(74) *Attorney, Agent, or Firm* — Kilpatrick Townsend & Stockton LLP

(57) ABSTRACT

A garment for providing orthopedic support or therapy to a human body may include a tubular flexible element and a tension strap. The tubular flexible element may be disposed around at least some portion of a human body and include flexible and a touch fastener portions. The flexible portion may be at an exterior of the tubular flexible element and cover a first portion of the body. The touch fastener portion may be at the exterior of the tubular flexible element and cover a second portion of the body. The tension strap may include first and second ends, where the first end includes a first touch fastener to be coupled with the touch fastener portion at a first location, and the second end includes a second touch fastener to be coupled with the touch fastener portion at a second location, thereby applying tension between the first and second locations.

19 Claims, 19 Drawing Sheets

Related U.S. Application Data continuation-in-part of application No. 14/829,867, filed on Aug. 19, 2015, now Pat. No. 10,285,842, which is a continuation of application No. 14/329,318, filed on Jul. 11, 2014, now abandoned.

(60) Provisional application No. 62/207,248, filed on Aug. 19, 2015, provisional application No. 61/928,847, filed on Jan. 17, 2014.

(51) Int. Cl.
  *A61F 5/02* (2006.01)
  *A61F 5/03* (2006.01)

(52) U.S. Cl.
  CPC .......... *A61F 5/0109* (2013.01); *A61F 5/0125* (2013.01); *A61F 5/02* (2013.01); *A61F 5/03* (2013.01); *A61F 5/30* (2013.01); *A61F 2005/0137* (2013.01); *A61F 2220/0025* (2013.01)

(58) Field of Classification Search
  CPC .......... A61F 5/0125; A61F 5/013; A61F 5/30; A61F 2005/0181; A61F 2005/0183
  See application file for complete search history.

(56) References Cited

U.S. PATENT DOCUMENTS

| | | |
|---|---|---|
| 4,089,064 A | 5/1978 | Chandler, Jr. |
| 4,287,885 A | 9/1981 | Applegate |
| 4,407,276 A | 10/1983 | Bledsoe |
| 4,502,301 A | 3/1985 | Swallow et al. |
| 4,624,247 A | 11/1986 | Ford |
| 4,697,583 A | 10/1987 | Mason et al. |
| 5,016,621 A | 5/1991 | Bender |
| 5,267,928 A | 12/1993 | Barile et al. |
| 5,277,698 A * | 1/1994 | Taylor ................ A61F 5/0123 602/16 |
| 5,575,010 A | 11/1996 | Chung |
| 5,836,904 A | 11/1998 | Cooper |
| 5,968,002 A | 10/1999 | Morrisseau |
| 7,122,016 B1 | 10/2006 | DeToro et al. |
| 8,162,867 B2 | 4/2012 | Nordt, III et al. |
| 8,357,111 B2 | 1/2013 | Caillouette et al. |
| 8,784,349 B1 | 7/2014 | Nelson |
| 10,285,842 B2 * | 5/2019 | Hodges, IV ......... A61F 5/0109 |
| 2004/0106887 A1 | 6/2004 | Schneider et al. |
| 2010/0082007 A1 | 4/2010 | Bobo |
| 2010/0292622 A1 * | 11/2010 | Weissleder ......... A61F 5/0193 602/23 |
| 2013/0296758 A1 | 11/2013 | Castillo |
| 2015/0051530 A1 | 2/2015 | Noda et al. |
| 2015/0119780 A1 | 4/2015 | DeLuke et al. |
| 2015/0202071 A1 | 7/2015 | Hodges et al. |
| 2015/0230959 A1 | 8/2015 | Gilmer et al. |
| 2015/0351945 A1 | 12/2015 | Hodges, IV et al. |
| 2016/0346153 A1 | 12/2016 | Hodges, IV |

* cited by examiner

SYSTEMS AND METHODS FOR ORTHOPEDIC SUPPORTS

CROSS-REFERENCE TO RELATED APPLICATIONS

This application is a continuation-in-part of U.S. patent application Ser. No. 15/242,139 filed Aug. 19, 2016, entitled, "SYSTEMS AND METHODS FOR ORTHOPEDIC SUPPORTS," which claims priority to Provisional U.S. Patent Application No. 62/207,248 filed Aug. 19, 2015, entitled "SYSTEMS AND METHODS FOR ORTHOPEDIC SUPPORTS," the entire disclosures of which are hereby incorporated by reference, for all purposes, as if fully set forth herein.

This application is also a continuation-in-part of U.S. patent application Ser. No. 14/829,867 filed Aug. 19, 2015, entitled "SYSTEMS AND METHODS FOR INCREASING THE EFFECTIVENESS OF A MECHANICAL JOINT BRACE," which is a continuation of U.S. patent application Ser. No. 14/329,318 filed Jul. 11, 2014, which claims priority and the benefit of U.S. Provisional Patent Application No. 61/928,847 filed Jan. 17, 2014, entitled "SYSTEMS AND METHODS FOR SECURING ORTHOPEDIC AND OTHER BRACES," the entire disclosures of which are hereby incorporated by reference, for all purposes, as if fully set forth herein.

BACKGROUND OF THE INVENTION

Embodiments of the invention relate generally to protective and/or therapeutic orthopedic wear. More specifically, embodiments of the invention relate to clothing which allows for customized application of protective and/or therapeutic elements to targeted areas of the body.

Current orthopedic support systems tend to be generic, sized for a variety of human beings, and designed to address a variety of orthopedic issues. Some current systems may support or protect a group of joints or muscles during athletic, occupational, or everyday activities. Other current systems may provide therapeutic value to a particular area of the body, and in the best cases possibly be provided for two to three size ranges of individuals.

This one, two, or three-size fits all approach, to both the individual concerned, and the joint or muscle area involved does not adequately take into account the almost infinite anatomic variation of individuals. Likewise, injuries or particular orthopedic needs of an individual user can also be infinitely varied. Current orthopedic garments are usually only readily available to address the most common of injuries and needs. Customization for the particular needs/injury of specific individuals are largely unaddressed unless the need/injury is very typical and the specific individual is of common shape and size.

Embodiments of the invention provide solutions to these and other problems in the prior art.

BRIEF DESCRIPTION OF THE INVENTION

In one embodiment, a garment for providing orthopedic support or therapy to a human body is provided. The garment may include a tubular flexible element and a tension strap. The tubular flexible element may be configured to be disposed around at least some portion of a human body and include a flexible portion and a touch fastener portion. The flexible portion may be at an exterior of the tubular flexible element and cover a first portion of the human body. The touch fastener portion may be at the exterior of the tubular flexible element and cover a second portion of the human body. The tension strap may include a first end and a second end, where the first end includes a first touch fastener configured to be coupled with the touch fastener portion at a first location, and the second end includes a second touch fastener configured to be coupled with the touch fastener portion at a second location, thereby applying tension between the first location and the second location.

BRIEF DESCRIPTION OF THE DRAWINGS

The present invention is described in conjunction with the appended figures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware, or microcode, the program code or code segments to perform the necessary tasks may be stored in a machine readable medium and a processor or processors may perform the necessary tasks.

Figure 1:
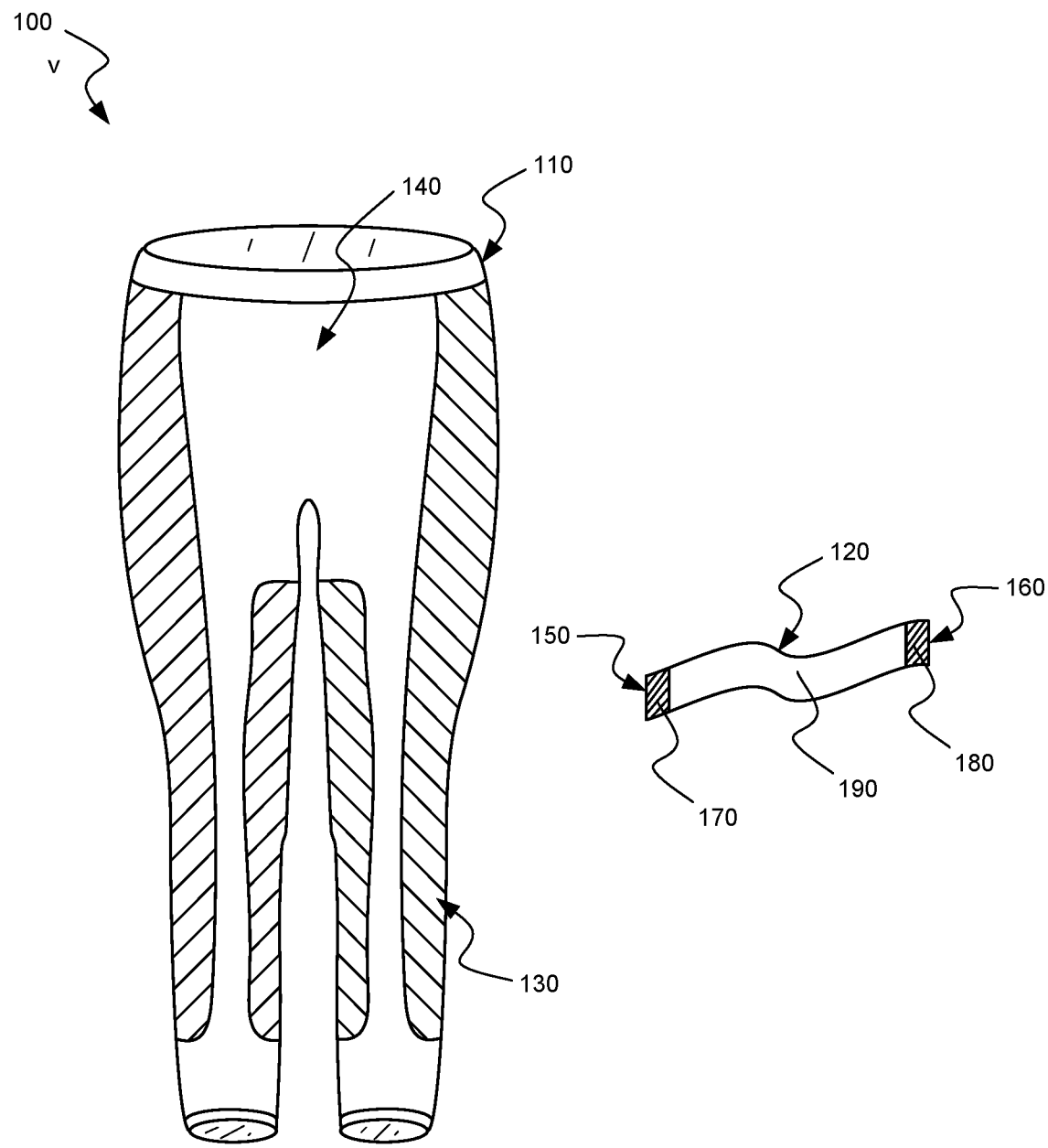
FIG. 1 is a schematic view of one garment of the invention, particularly a pair of pants, which provides means for orthopedic support and therapy to be applied to a wearer.
Figure 2A:
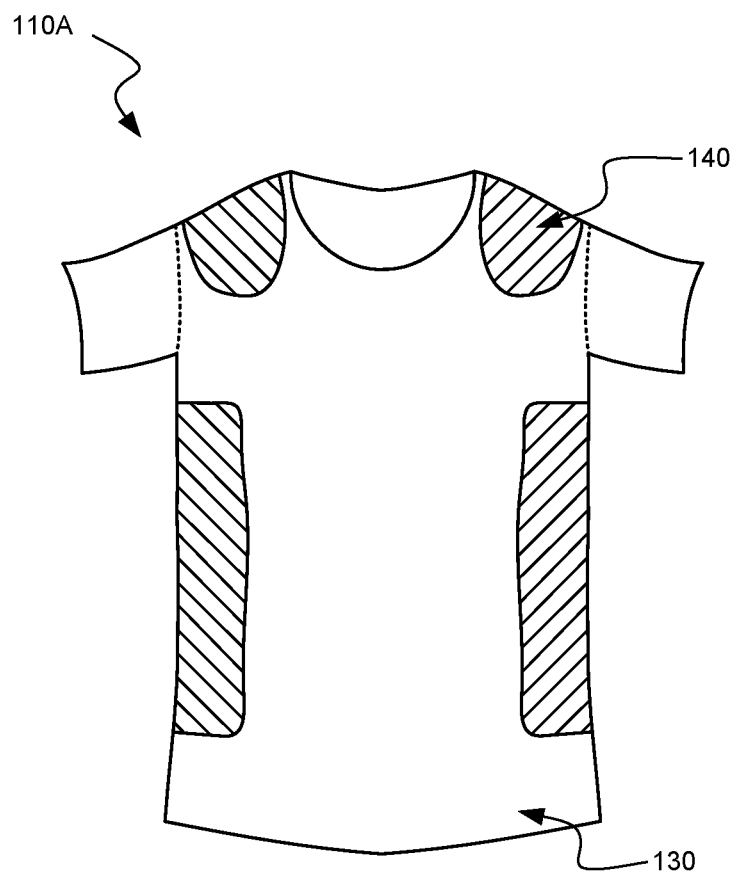
FIG. 2A is a schematic view of another garment of the invention, particularly a shirt, which provides means for orthopedic support and therapy to be applied to a wearer.
Figure 2B:
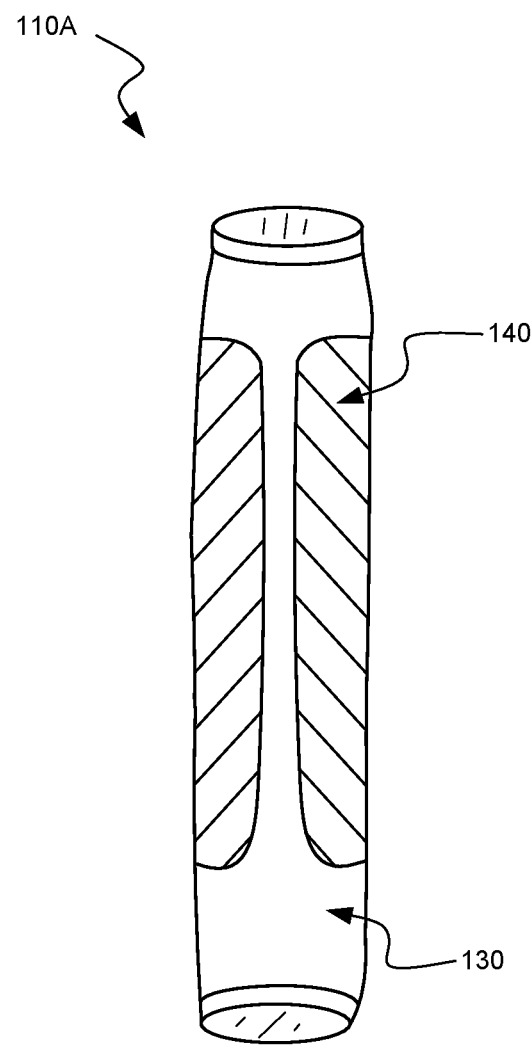
FIG. 2B is a schematic view of another garment of the invention, particularly a tubular sleeve, which provides means for orthopedic support and therapy to be applied to a wearer.
Figure 2C:
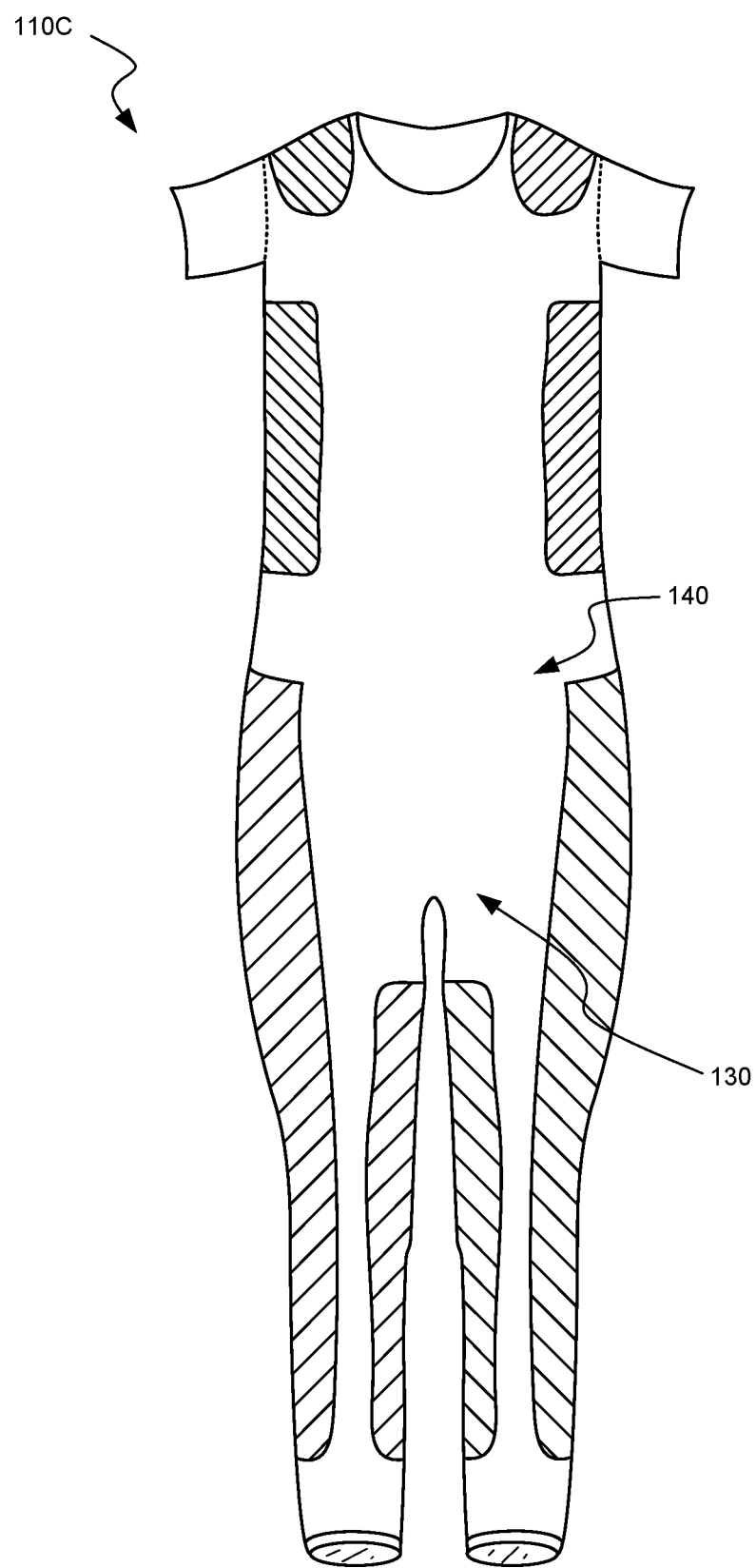
FIG. 2C is a schematic view of another garment of the invention, particularly a bodysuit, which provides means for orthopedic support and therapy to be applied to a wearer.

Turning to FIG. 1, in one embodiment of the invention, a garment 100 for providing orthopedic support or therapy to a human body is provided. Garment 100 may include a tubular flexible element 110 and a tension strap 120. Though tubular flexible element 110 is shown in this embodiment as a pair of pants, in other embodiments, as shown in FIG. 2A-C, tubular flexible element 110 could be a sleeved or sleeveless shirt 110A; a tubular sleeve 110B for an arm, leg, or other joint area; or a body suit 110C. Tubular sleeve 110B, or other shaped garments, may allow for the garment to be used at various joints or locations on the body. Merely by way of example, tubular sleeve may be worn by a user around their elbow, shin/calf, Achilles tendon, ankle, shoulder, wrist, neck, and in larger versions around some portion of the back, hip, torso, sternum, waist, thighs, etc. Other shapes of garments are also possible within the scope of this disclosure.

Tubular flexible element 110 may be configured to be disposed around at least some portion of a human body and include a flexible portion 130 and a touch fastener portion 140. Flexible portion 130 may be at an exterior of tubular flexible element 110 and cover a first portion of the human body. Touch fastener portion 140 may also be at the exterior of tubular flexible element 110 and cover a second portion of the human body. In other words, portions of the exterior of tubular flexible element 110 will consist of flexible portion 130, while remaining portions of the exterior consist of touch fastener portion 140. In some embodiments, flexible portion 130 and/or material thereof, may also underlie touch fastener portion 140. In other embodiments, a different material may underlie touch fastener portion 140.

Flexible portion 130 may include neoprene and/or other flexible materials such as polyesters, nylon, lycra, spandex, rayon, etc. which are flexible. In some embodiments, flexibility may be multidirectional, while in other embodiments, flexibility may be unidirectional. In yet other embodiments, combinations of the same will be present, either through the use of a consistent material, or combinations of materials.

Touch fastener portion 140 may include Dual Lock™, Velcro™ or other hook and loop material, and/or any other touch fastener material which allows for two materials to be coupled to each other by pressing or applying them against each other. Touch fastener portion 140 may consist of the loop element of the hook and loop or hook and loop-like material so as not to unintentionally attract fabric to attach to the garment.

Tension strap 120 may include a first end 150 and a second end 160. First end 150 may include a first touch fastener 170 configured to be coupled with touch fastener portion 130 at a first location (for example, anywhere within touch fastener portion 140). In the embodiment described, first touch fastener 170 may be the hook element of hook and loop (or the like) material, so as to mate with a loop element of touch fastener portion 140. Second end 160 may include a second touch fastener 180 configured to be coupled with touch fastener portion 140 at a second location (for example, a different location than where first touch fastener 170 is coupled with touch fastener portion 140), thereby applying tension between the first location and the second location, or at least limiting the movement of the two locations of tubular flexible element 110 away from each other if the limit of the elasticity of tension strap 120 is reached. Thus for example, if a particular tensions strap 120 is of fixed length (non-flexible), tension will be applied by the strap when movement of the two locations attempts to exceed the fixed length of tensions strap 120.

Figure 3:
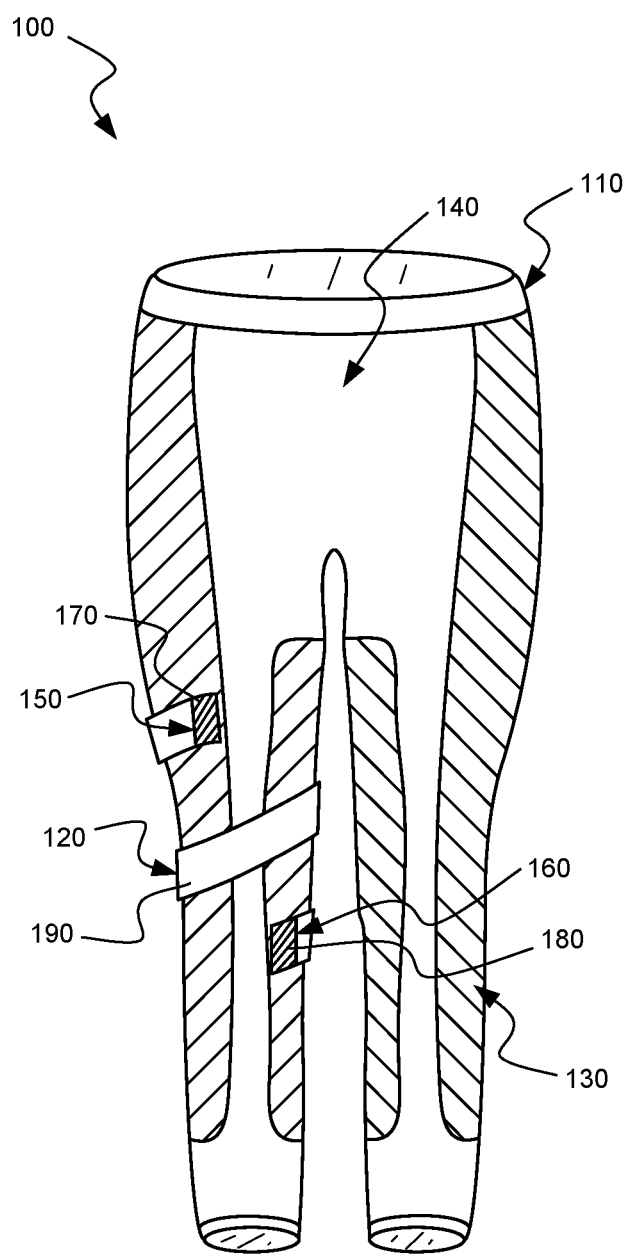
FIG. 3 is a schematic view of the garment from FIG. 1 where the tension strap has been applied to the tubular flexible element.

Merely by way of example, one example positioning of tension strap 120 on tubular flexible element is shown in FIG. 3, where tension strap 120 has been coupled at one end below the knee of the pants, wrapped around the leg of the pants, and then coupled at the other end above the knee.

Though FIGS. 1 and 2A-C show flexible portion 130 and touch fastener portion 140 in certain specific areas of the particular garment therein, one of skill in the art will now understand, based on the contents of this disclosure, that flexible portion 130 and touch fastener portion 140 could be arranged differently than shown. In some embodiments flexible portion may take up more or less of a garment than shown, and be provided in different shaped areas thereon. Likewise, in these or other embodiments, touch fastener portion 140 may take up more or less of a garment than shown, and be provided in different shaped areas thereon. Ideally, the garment will remain flexible because of the presence of adequate flexible portion 130 areas, but provide touch fastener portion 140 in as many areas as necessary to provide means to configure tension strap 120 in any manner desired, thereby providing maximum customized configurations for different sized users and different therapeutic/protective needs.

In the embodiment shown in FIG. 3, second touch fastener 180 may be the hook element of hook and loop material, so as to mate with a loop element of touch fastener portion 140. In various embodiments, first and second touch fasteners 170, 180 may be located on one or both sides of tension strap 120. In some embodiments, one side of tension strap 120 may have hook elements of a hook and loop material at first and second touch fasteners 170, 180, while the other side of tensions strap may have loop elements of a hook and loop material, thereby allowing additional elements (e.g., tension straps or other elements) to be coupled with the outside portion of first and second touch fasteners 170, 180.

Tension strap 120 may also include an intermediate portion 190 between first end 150 and second end 160 by which the construction characteristics thereof change the overall elasticity characteristics of tension strap 120. Merely by way of example, intermediate portion 190 could be constructed of an inelastic material, thereby setting a maximum length of tension strap 120. This may be referred to herein as a fixed length assembly. Alternatively, intermediate portion 190 could be constructed of an elastic material, thereby setting a default length of tension strap 120 (an un-stretched length), but allowing for a maximum potential length greater than the default length (a fully stretched length). This may be referred to herein as a variable length assembly. In such an embodiment, the spring rate of the elastic material used in intermediate portion 190 could be varied to achieve different strengths of feedback on the user when tension strap 120 is stretched between its coupling points on touch fastener portion 140.

In these or other embodiments, intermediate portion 190 may also include a third touch fastener on the same and/or different side than the first and second touch fastener 170, 180 elements which couple with the touch fastener portion 140. Such a third touch fastener may only be present in a certain location or locations on the underside of intermediate portion 190. In such embodiments, when tension strap 120 is coupled with garment 100, the tension between first touch fastener 170 and third touch fastener could be varied from the tension provided between third touch fastener and second touch fastener 190. Thus, for example, the spring rate in the construction between first touch fastener 170 and third touch fastener could be higher or lower than the spring rate between third touch fastener and second touch fastener 190.

Alternatively or in addition to the above, having a third touch fastener on an exterior of tension strap 120 may allow for additional tension straps to be coupled onto the top of tensions strap 120. Any number of tensions straps 120 may be present in a given embodiment, either at the same, different, or overlapping locations depending on the locations in which the user desires to have additional orthopedic support. Also, while tension strap 120 is shown as being a constant width along its length, in some embodiments the width of tension strap 120 may vary along the length, including being wider at one end than the other in order to provide more tension across a greater area as necessary in a particular therapeutic scenario.

Figure 4:
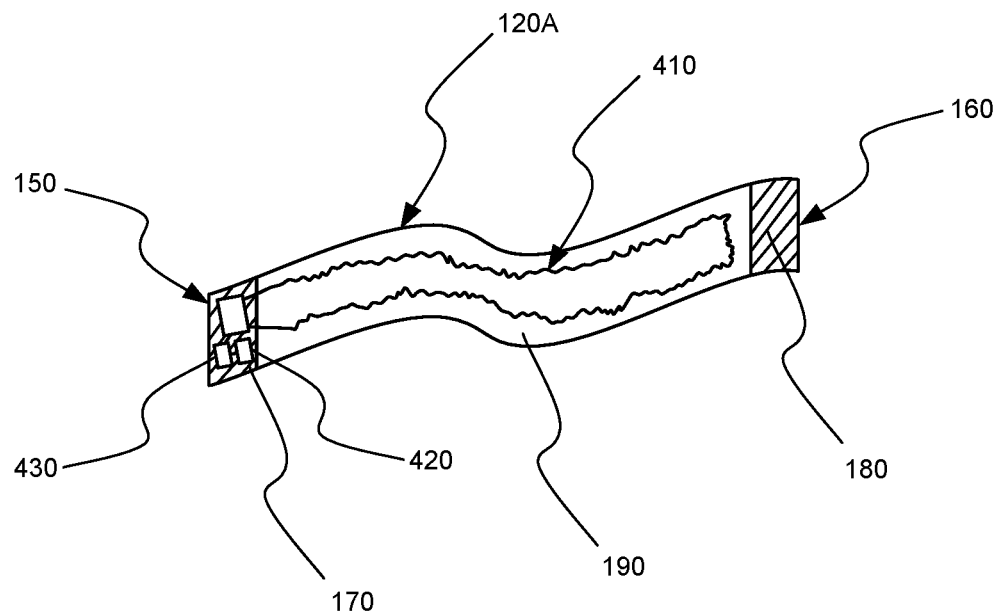
FIG. 4 is a schematic view of an alternative tension strap of the invention having electronics included therewith.

In some embodiments, as shown in FIG. 4, tension strap 120A may include a tension detector 410 disposed on or within intermediate portion 190 for measuring tension between first end 150 and second end 160. An accelerometer 420, gyroscope, and/or other movement detecting device may also be included for determining acceleration, speed, and/or direction of movement of tension strap 120A, and thus acceleration/movement of that particular location on the wearer of garment 100. A communication device 430, employing Bluetooth, WiFi, or other wireless communication medium, may allow for transmission of information from tension detector 410, accelerometer 420, gyroscope, or other movement detecting device to a remote processor/storage device for analysis. Wired communication methods may also be available to communicate data to a remote storage unit and/or processor, perhaps after the data is temporarily stored on a device within tensions strap 120A.

Figure 5:
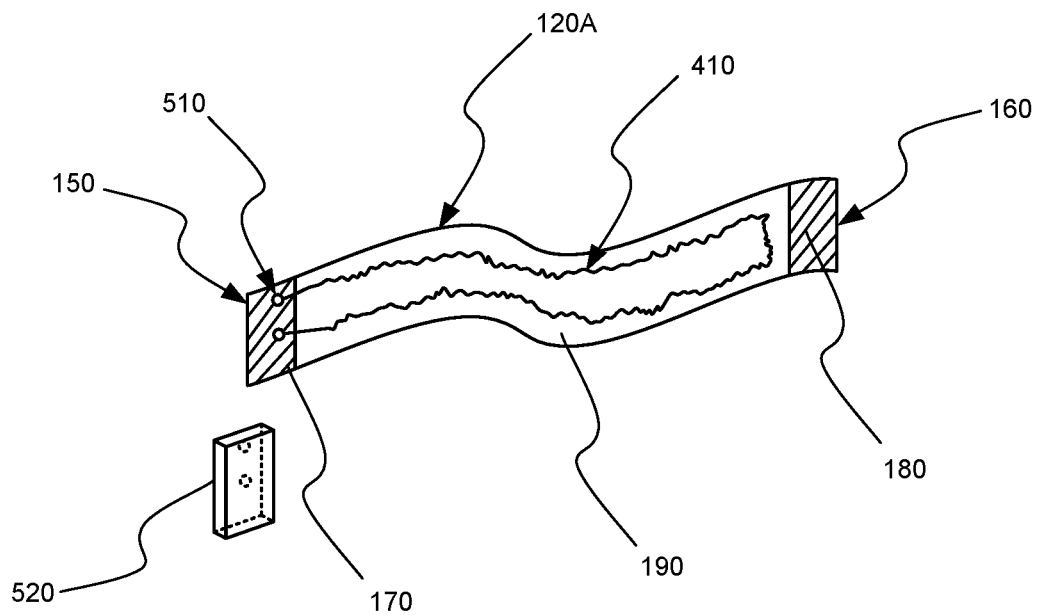
FIG. 5 is a schematic view of an alternative tensions strap of the invention having a detachable electronics package.

In another similar embodiment, as shown in FIG. 5, tension strap 120B may also include electrical leads 510 which allows for a detachable electronics package 520 to be connected with tension strap 120B. Detachable electronics package 520 may include at least a portion of a tension detector 410 for measuring tension between the first end and the second end, as well as an accelerometer 420, gyroscope, and/or other movement detecting device. A communication device may also be present for either wired or wireless communication to a remote storage unit and/or processor for analysis of the data.

In some embodiments, a compression detector may also be present in tubular flexible element 110, or more commonly, in tension strap 120. The compression detector may allow for determining the amount of compression being applied to the user at a given point on tubular flexible element 110 or tension strap 120. Data from the compression detector may be passed on to remote storage/processors through communication means as described above with regard to tension detector 410, accelerometer 420, gyroscope, and/or other movement detecting device.

In addition to the aforementioned features, garment 100 may also include and feature described by co-pending U.S. patent application Ser. No. 14/829,867, entitled, "SYSTEMS AND METHODS FOR INCREASING THE EFFECTIVENESS OF A MECHANICAL JOINT BRACE," the entire disclosure of which is hereby incorporated by reference, for all purposes, as if fully set forth herein. Furthermore, any feature described therein may be detachable from garment 100 via touch fastening portion 130.

Likewise, any feature mentioned in co-pending U.S. patent application Ser. No. 15/167,548, entitled "SYSTEMS AND METHODS FOR THERAPEUTIC STIMULATION VIA GARMENTS AND INSERTS PROVIDED THEREON," may also be included in garment 100. The entire disclosure of the aforementioned application is hereby incorporated by reference, for all purposes, as if fully set forth herein. Any feature described therein may also be detachable from garment 100 via touch fastening portion 130.

Figure 6:
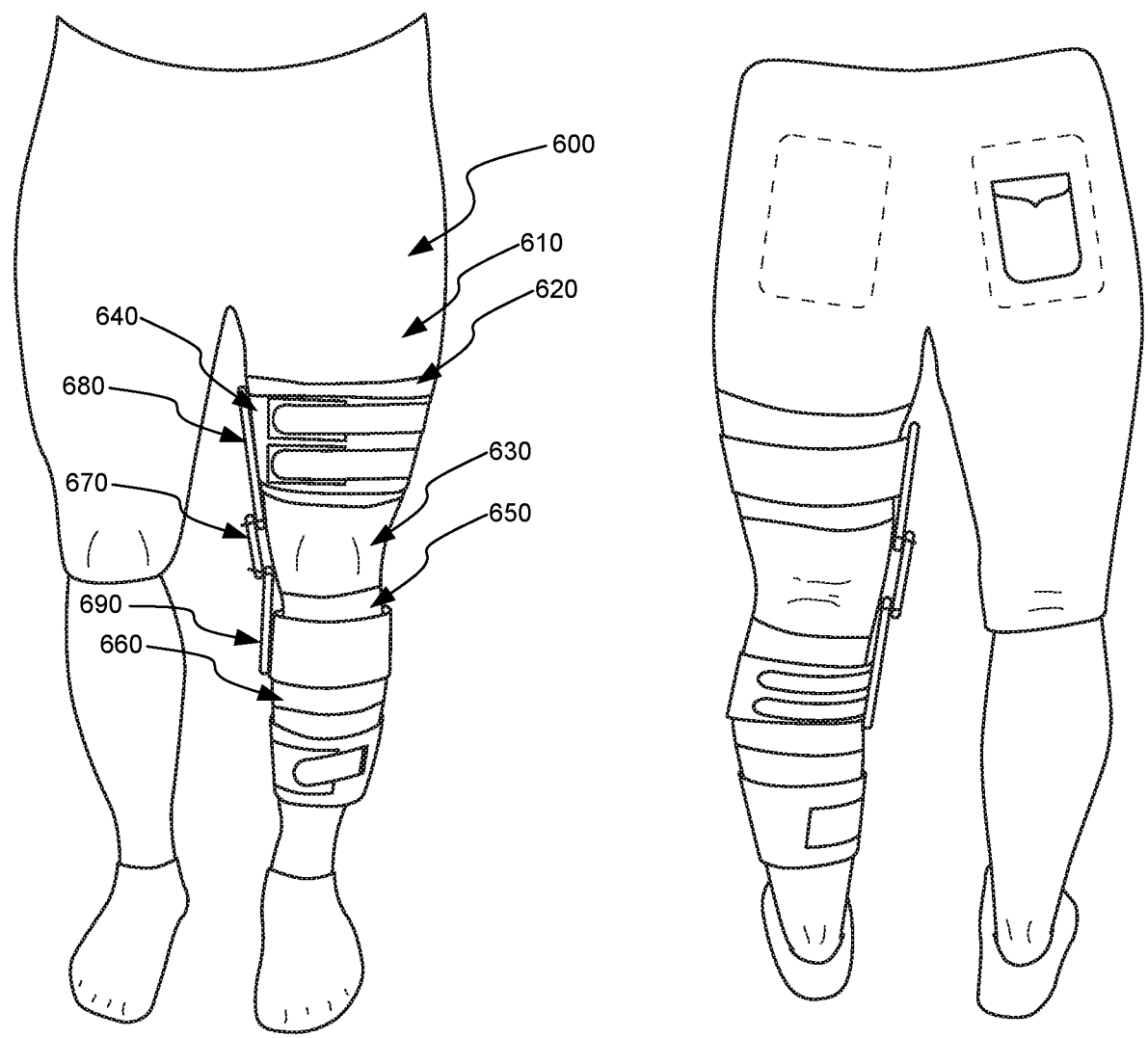
FIG. 6 is a schematic view of a sleeve and single hinge/axis mechanical joint brace of the invention.
Figure 7:
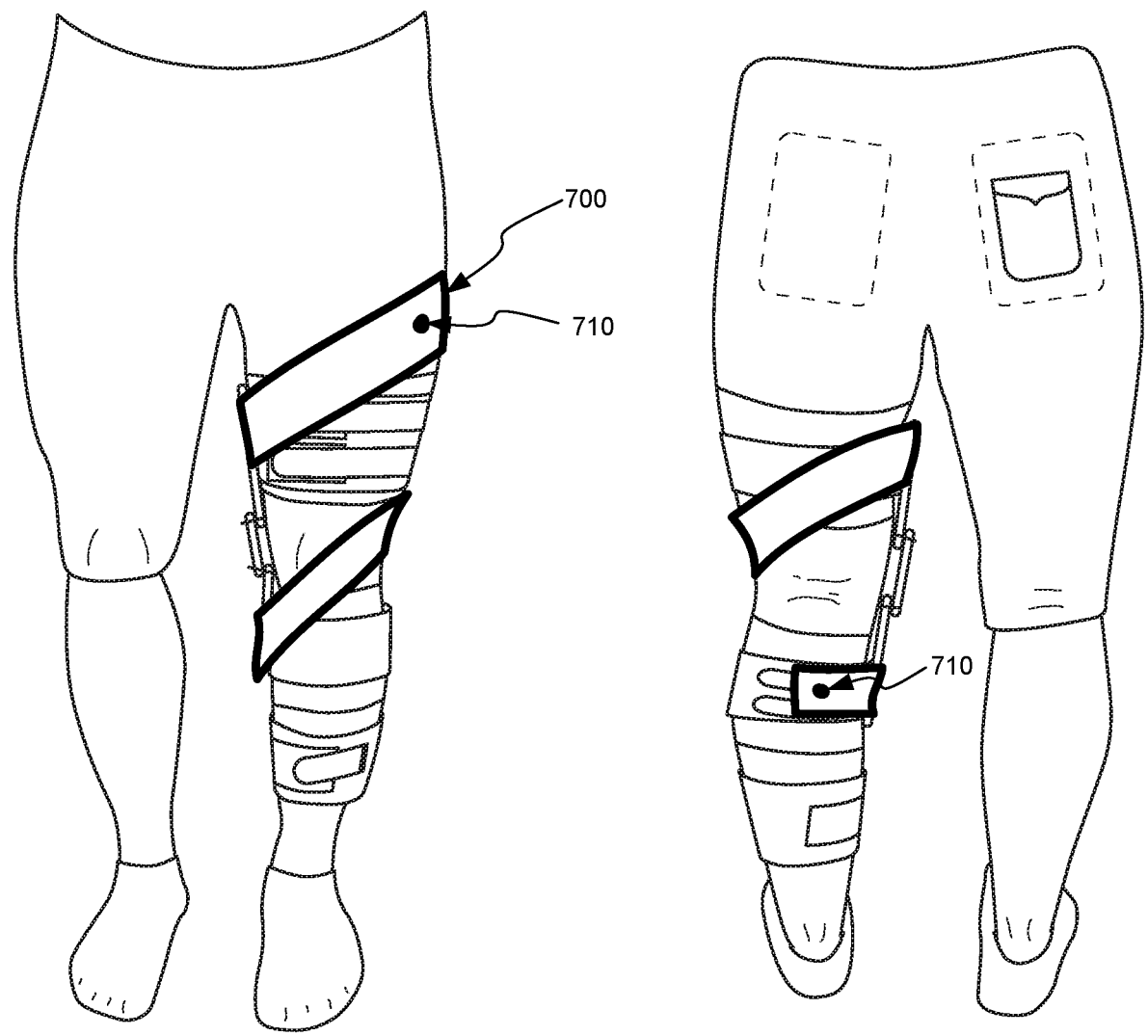
FIGS. 7-10 are schematic views of particular embodiments of the invention where an elastic strap is coupled with a lower portion of a mechanical joint brace, and an upper portion of the sleeve.
Figure 8:
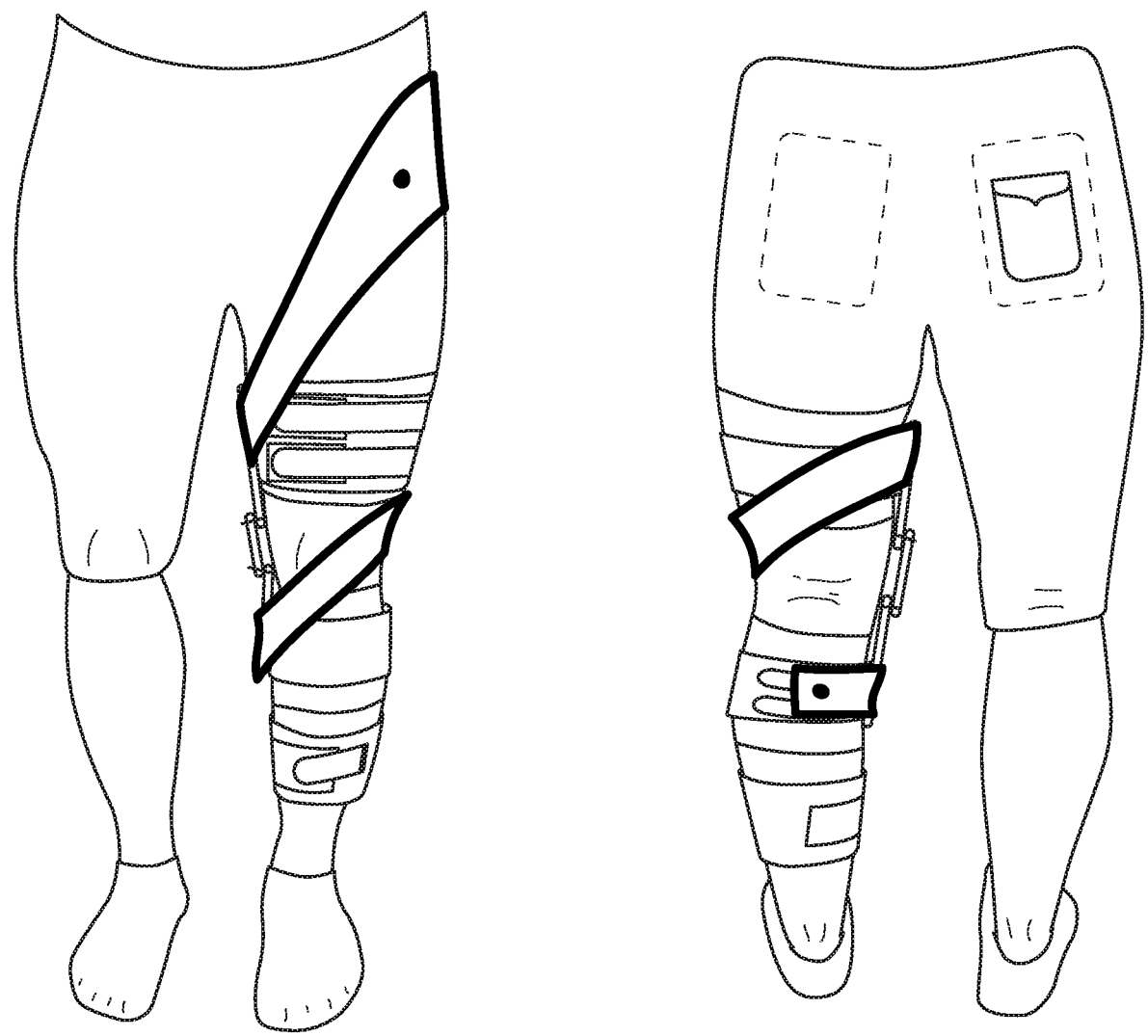
Figure 9:
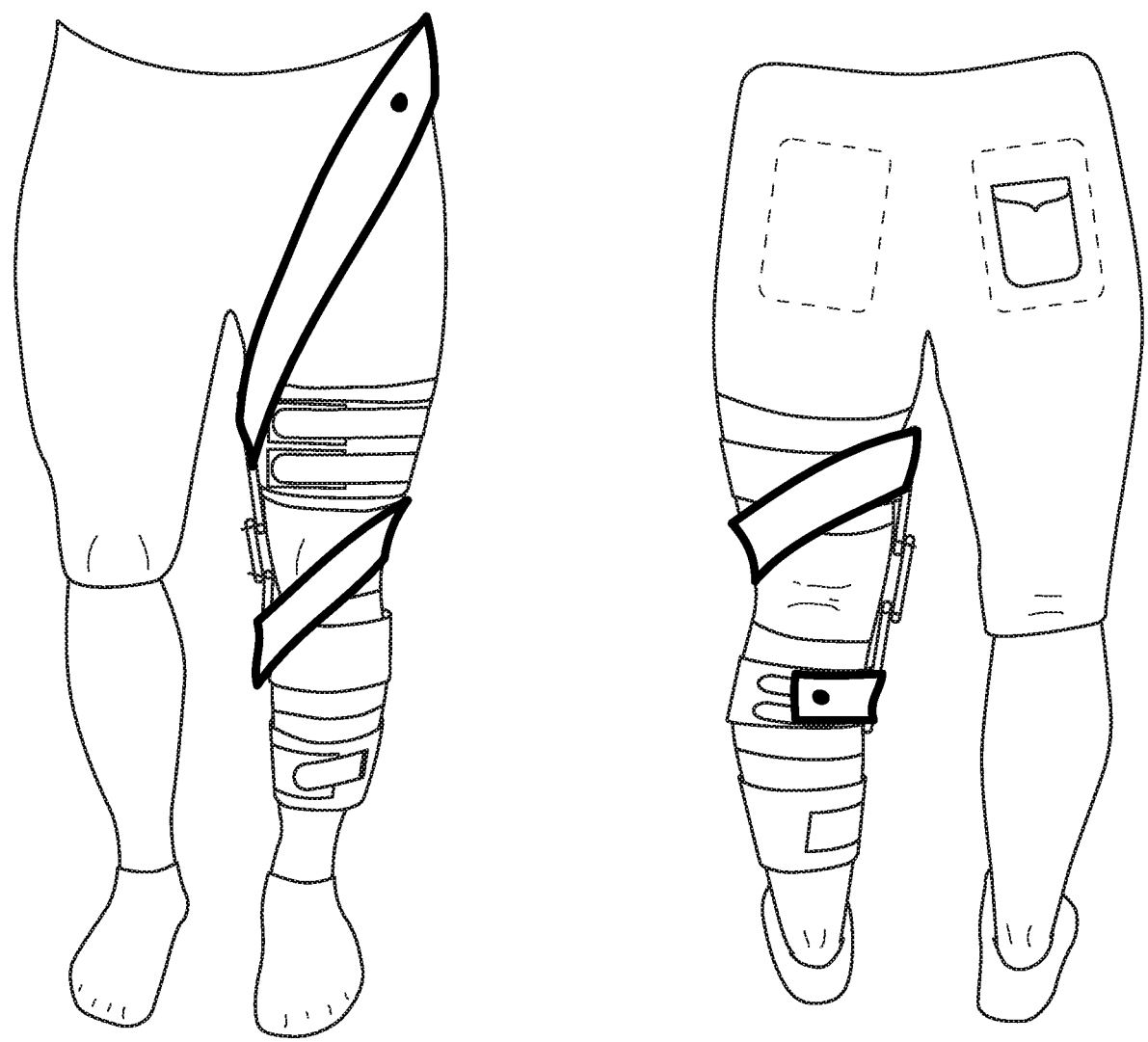
Figure 10:
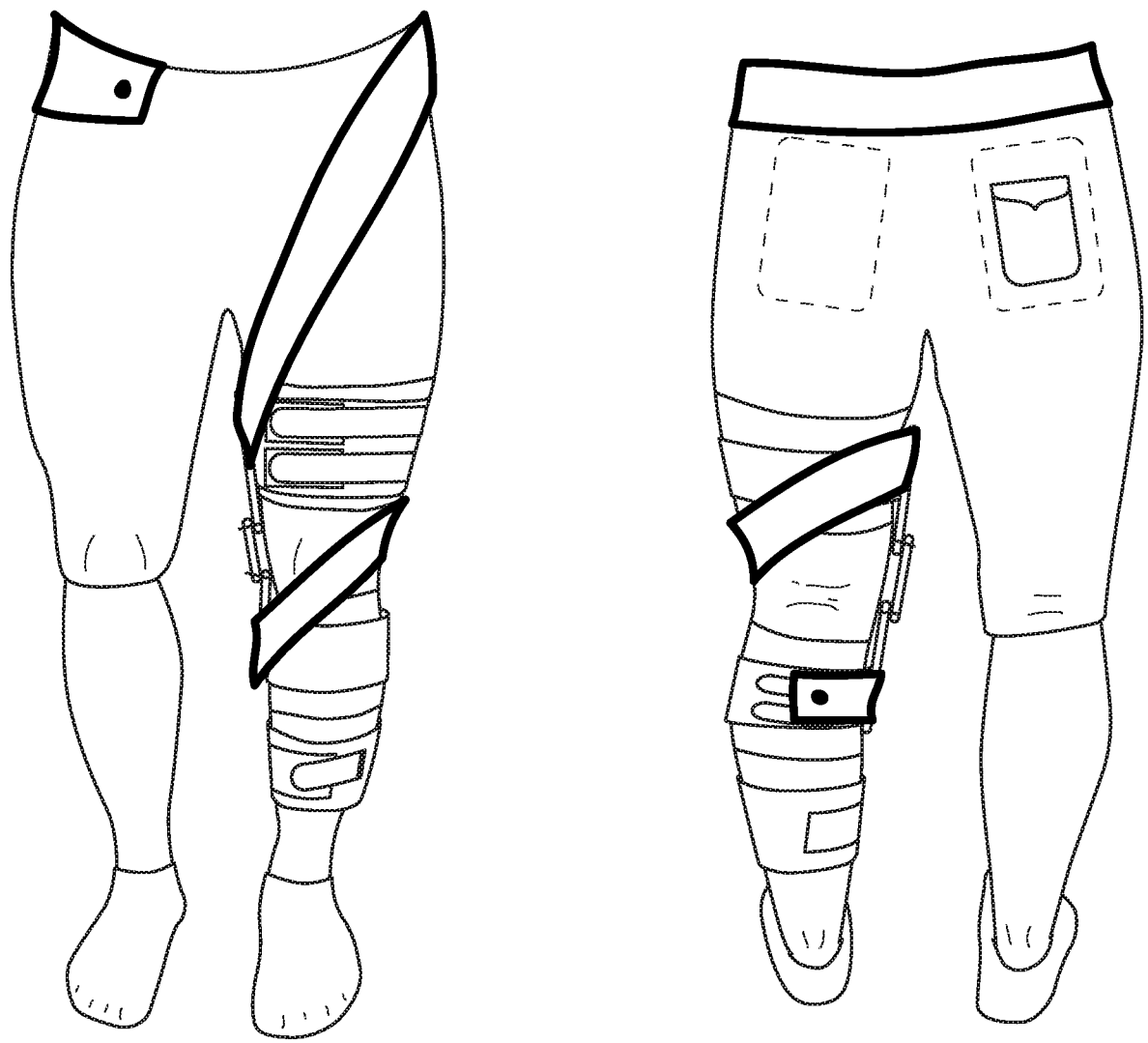

In another embodiment, another method for providing orthopedic support or therapy to a human body is disclosed. With reference to FIG. 6, the method may include disposing a sleeve 600 (similar to a pair of tight pants) over a leg 610 of a user such that a first portion 620 of sleeve 600 applies compressive pressure to leg 610 above a knee 630, wherein first portion 620 of sleeve 600 includes a first set of one or more pads 640 at least partially encircling leg 610 above knee 630. A second portion 650 of sleeve 600 applies compressive pressure to leg 610 below knee 630, wherein second portion 650 of sleeve 600 includes a second set of one or more pads 660 at least partially encircling leg 610 below knee 630. The method may also include disposing and tightening a mechanical joint brace 670 over sleeve 600. A first portion 680 of mechanical joint brace 670 compresses the first set of one or more pads 640 of sleeve 600 between first portion 620 of mechanical joint brace 670 and leg 610 above knee 630, and a second portion 690 of mechanical joint brace 670 compresses the second set of one or more pads 660 of sleeve 600 between the second portion 690 of mechanical joint brace 670 and leg 610 below knee 630. The method may finally include coupling a first end of an elastic strap with some portion of the sleeve, and coupling a second end of the elastic strap with some portion of the mechanical joint brace (see FIGS. 7-11). More specific embodiments are discussed below.

In many embodiments, the mechanical joint brace has only one hinge which rotates about an axis passing through the knee. In many embodiments, the hinge may be located on the inside of the knee, proximate to the other knee of the user. In other embodiments, the hinge may be located on the outside of the knee, distal to the other knee of the user. In other embodiments two hinges which rotate about an axis or axes passing through the knee may be employed.

In some embodiments, the elastic straps may be characterized by having between about 30% and about 60% elasticity, meaning they can be stretched from their un-stretched state to have an additional 30% to 60% length. In some specific embodiments, the elasticity may be about 30%, about 35%, about 40%, about 45%, about 50%, about 55%, or about 60%. Coupling of a strap to the sleeve and/or mechanical joint brace may be achieved via hook and loop fasteners (i.e., Velcro™), button snaps, and/or any other method known in the art. In other words, both the sleeve and the mechanical joint brace may have fastening systems located at one more portions thereof to enable to couplings described herein. In some embodiments, one or more straps discussed herein may be pre-attached (fixedly coupled) at either end to the mechanical joint brace or the sleeve.

In one embodiment, the first end of the elastic strap may be coupled with the sleeve proximate to a hip of the user, and the second end of the elastic strap may be coupled with the second portion of the mechanical joint brace. The elastic strap may wrap around a longitudinal axis of the leg at least once or twice. Proximate to the hip of user many include a side of the hip, a side of a thigh below the hip, or a side of the waist above the hip. In other embodiments, the first end of the elastic strap may be coupled with the sleeve at any point around the waist of the user.

FIGS. 7-10 show variations of the above discussed embodiments, where an elastic strap 700 at a first end 710 is coupled with a sleeve at various locations, and at a second end 720 with mechanical joint brace. In at least these embodiments, the elastic strap may work to counteract rotation of the knee inward, thereby preventing injury, reducing aggravation of injuries, and/or strengthening rotational control of the knee by the user.

Figure 11:
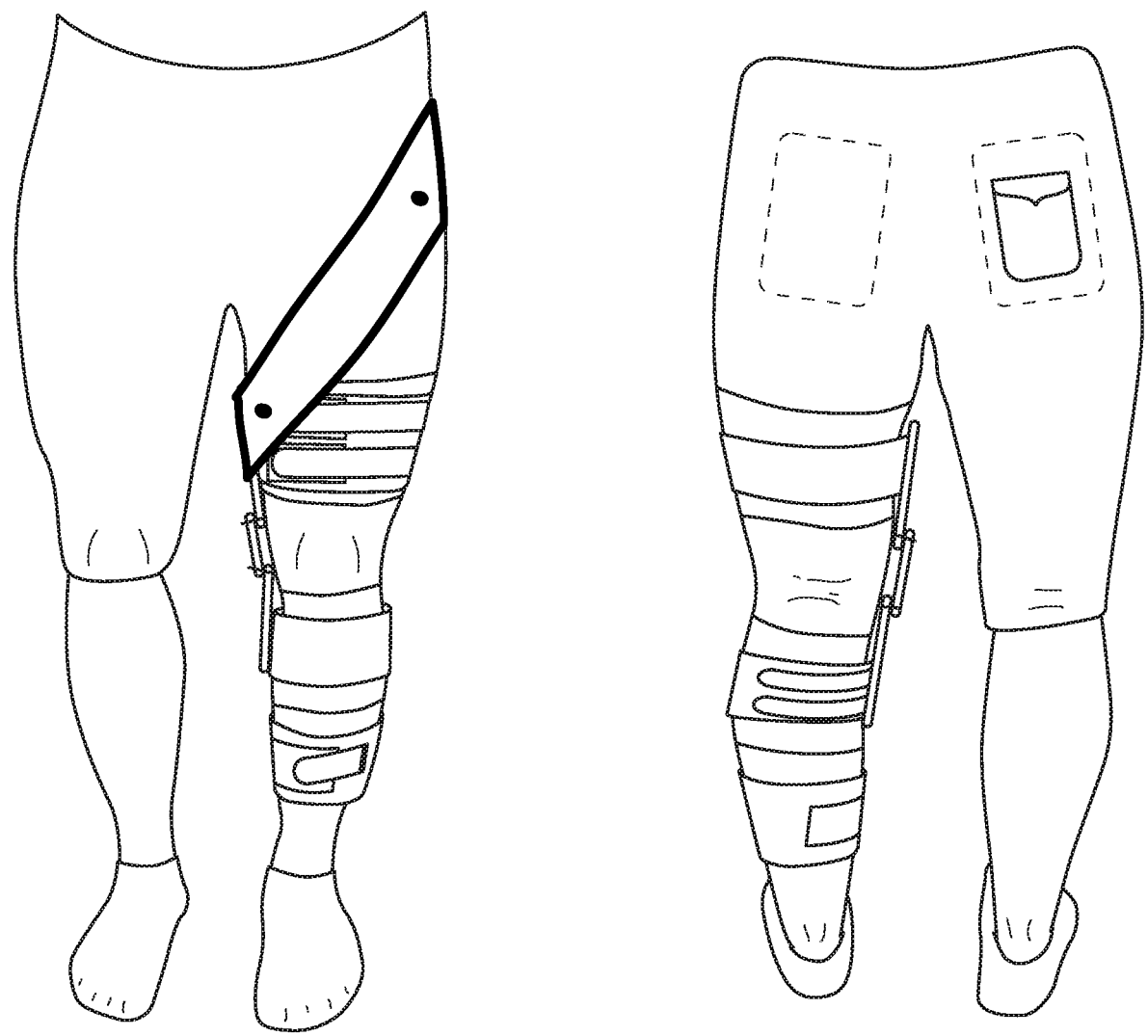
FIGS. 11 and 12 are schematics view of other particular embodiments of the invention where an elastic strap is coupled with an upper portion of a mechanical joint brace, and an upper portion of the sleeve.

FIG. 11 shows another embodiment where the first end of the elastic strap is coupled with the sleeve proximate to a hip of the user, and the second end of the elastic strap is coupled with the first portion of the mechanical joint brace at an inside of a thigh of the leg.

Figure 12:
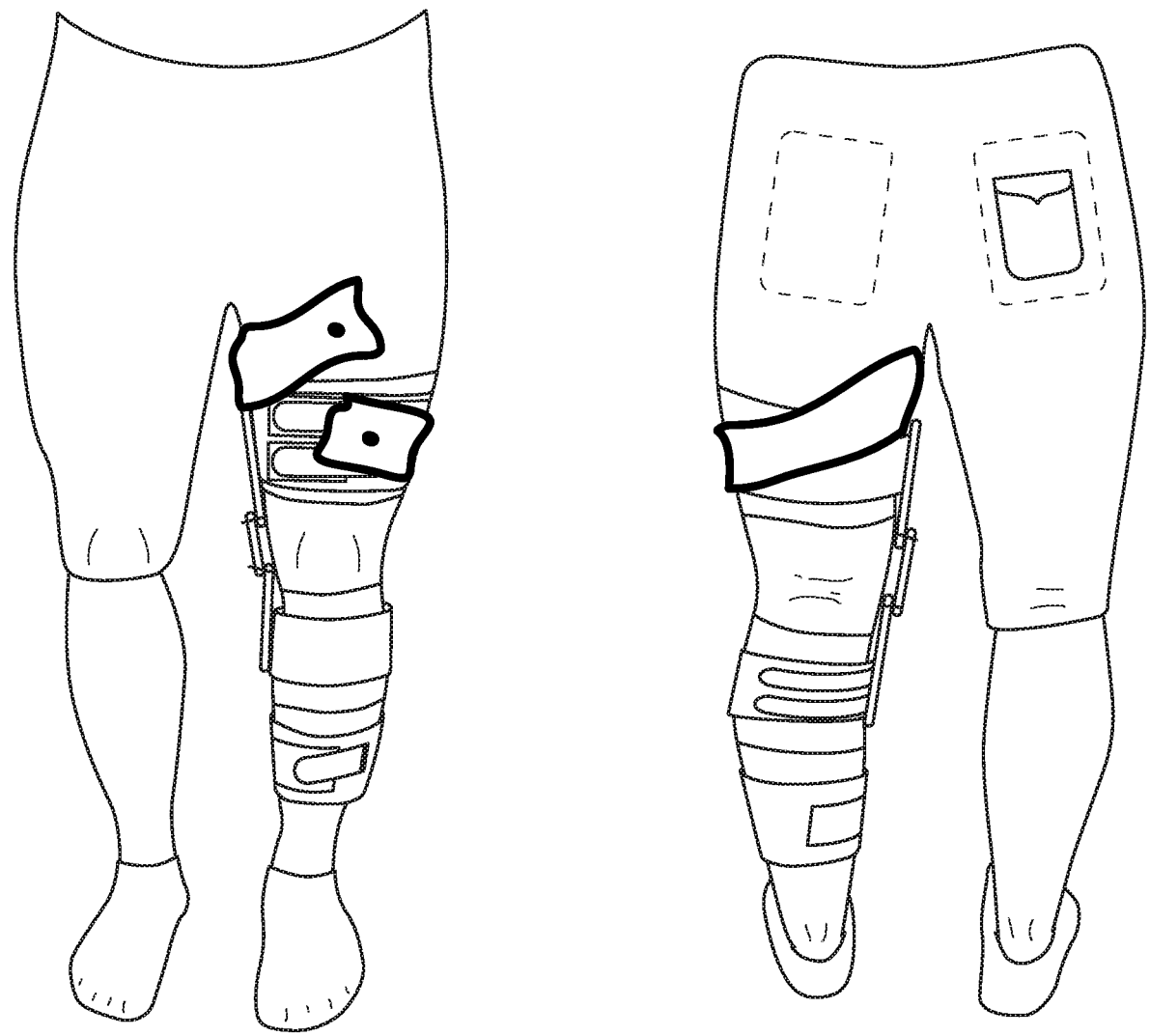

FIG. 12 shows another embodiment where the first end of the elastic strap is coupled with the sleeve above the knee, while the second end of the elastic strap is coupled with the first portion of the mechanical joint brace. The elastic strap wraps around a longitudinal axis of the leg at least once.

Figure 13:
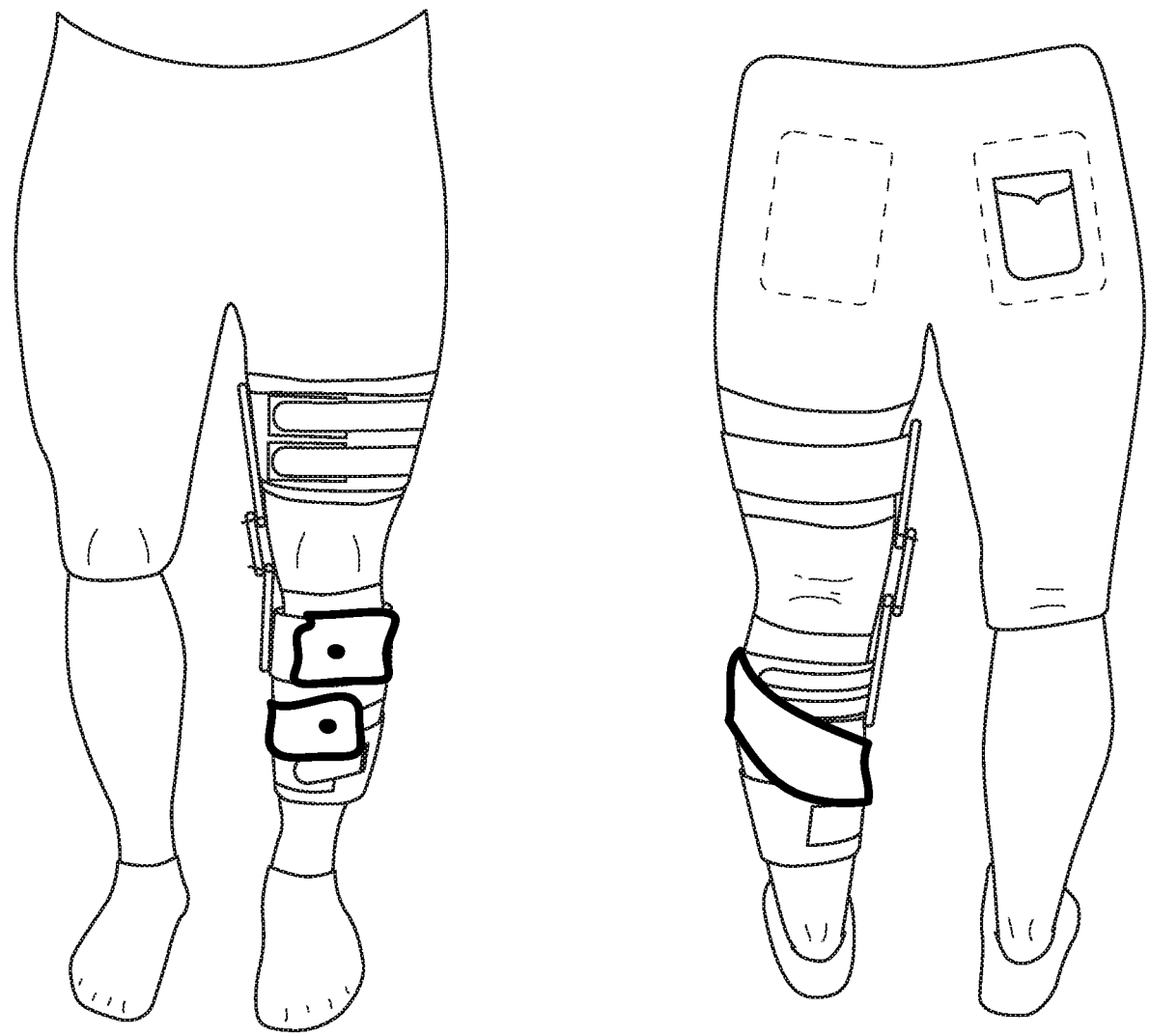
FIG. 13 is a schematic view of another particular embodiment of the invention where an elastic strap is coupled with a lower portion of a mechanical joint brace, and a lower portion of the sleeve.

FIG. 13 shows another embodiment where the first end of the elastic strap is coupled with the sleeve below the knee, while the second end of the elastic strap is coupled with the second portion of the mechanical joint brace. The elastic strap wraps around a longitudinal axis of the leg at least once.

Figure 14:
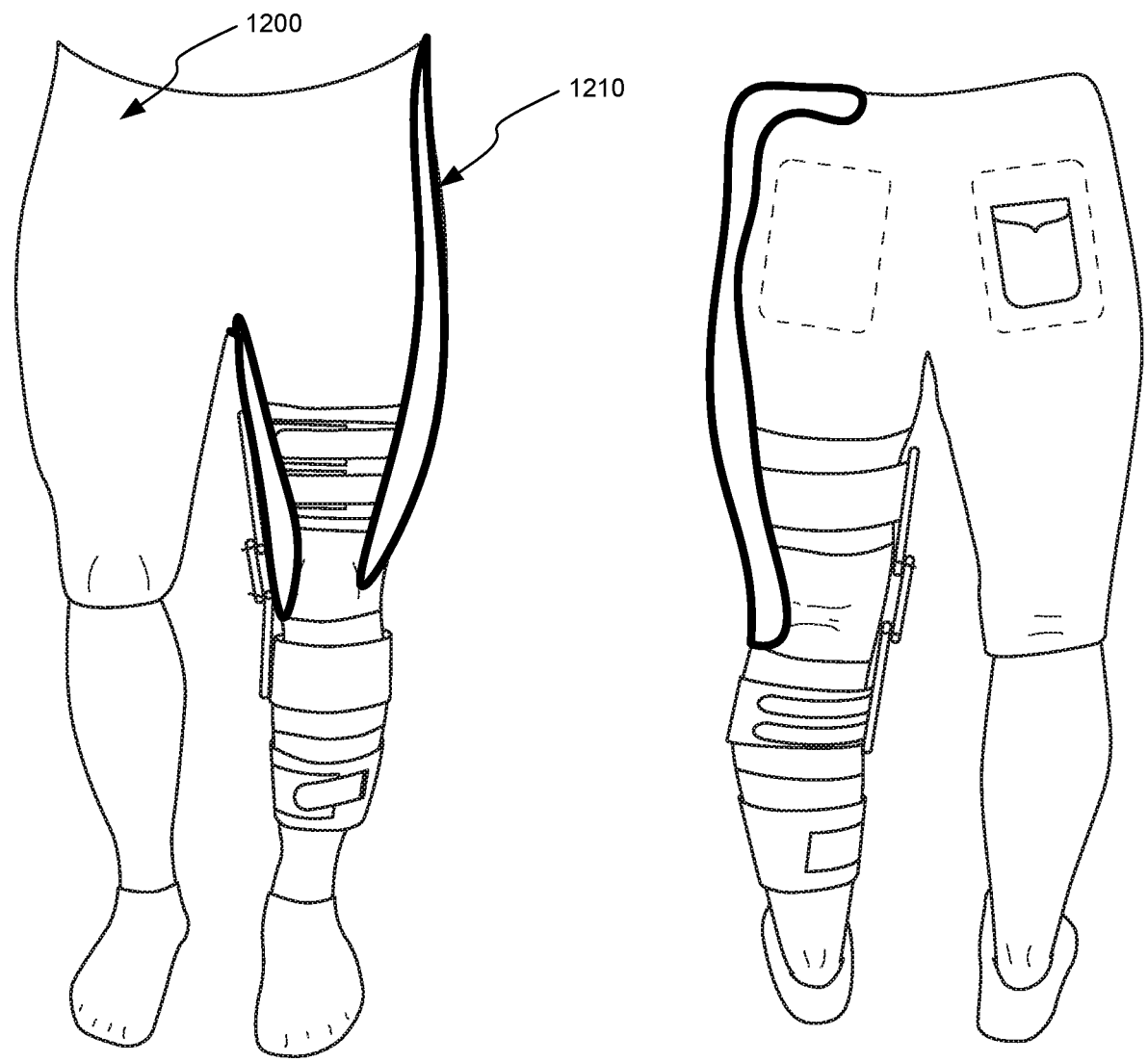
FIG. 14 is a schematic view of a particular padded sleeve employed by various embodiments of the invention.

FIG. 14 shows a slightly modified sleeve 1200 that may be employed in some embodiments of the invention. Modified sleeve 1200 may include padding 1210 both at an inner portion of the leg, as well as an outer portion of the leg as shown. The padding may assist in "gripping," or providing comfort from, a strap disposed as otherwise disclosed above.

Figure 15:
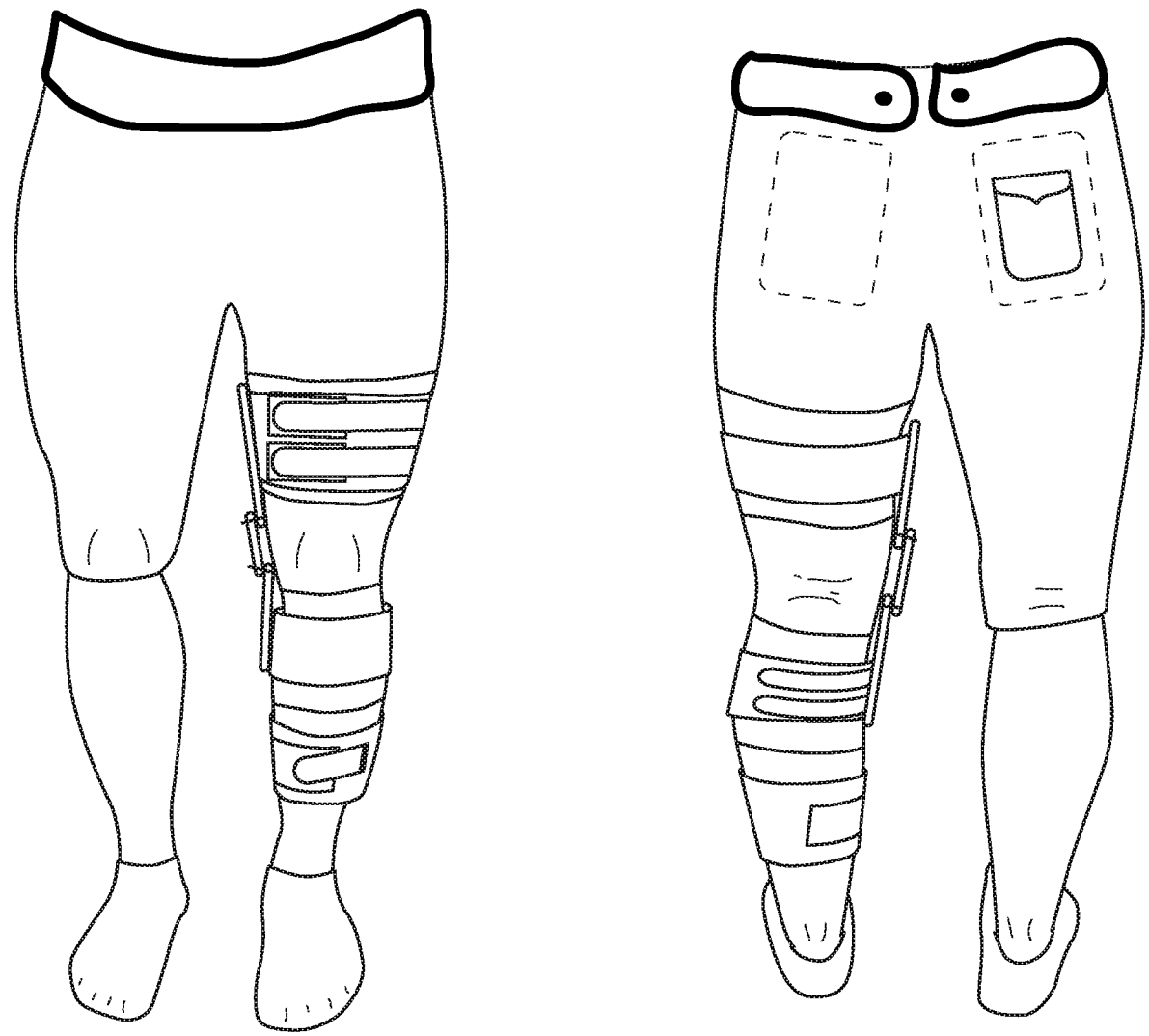
FIG. 15 is a schematic view of a secondary elastic strap employed by various embodiments of the invention.

In some embodiments, a second elastic strap may also be employed. The second elastic strap may couple at a first end with at least some portion of the mechanical joint brace or the sleeve, and at a second end with at least some portion of the mechanical joint brace or the sleeve. In some embodiments, the second elastic strap may be less elastic than the first elastic strap (for example, between 0% and 20% elasticity), and wrap substantially horizontally around a portion of the user. An example of one possible location is shown in FIG. 15, where the second elastic strap wraps substantially around the waist of the user.

Figure 16:
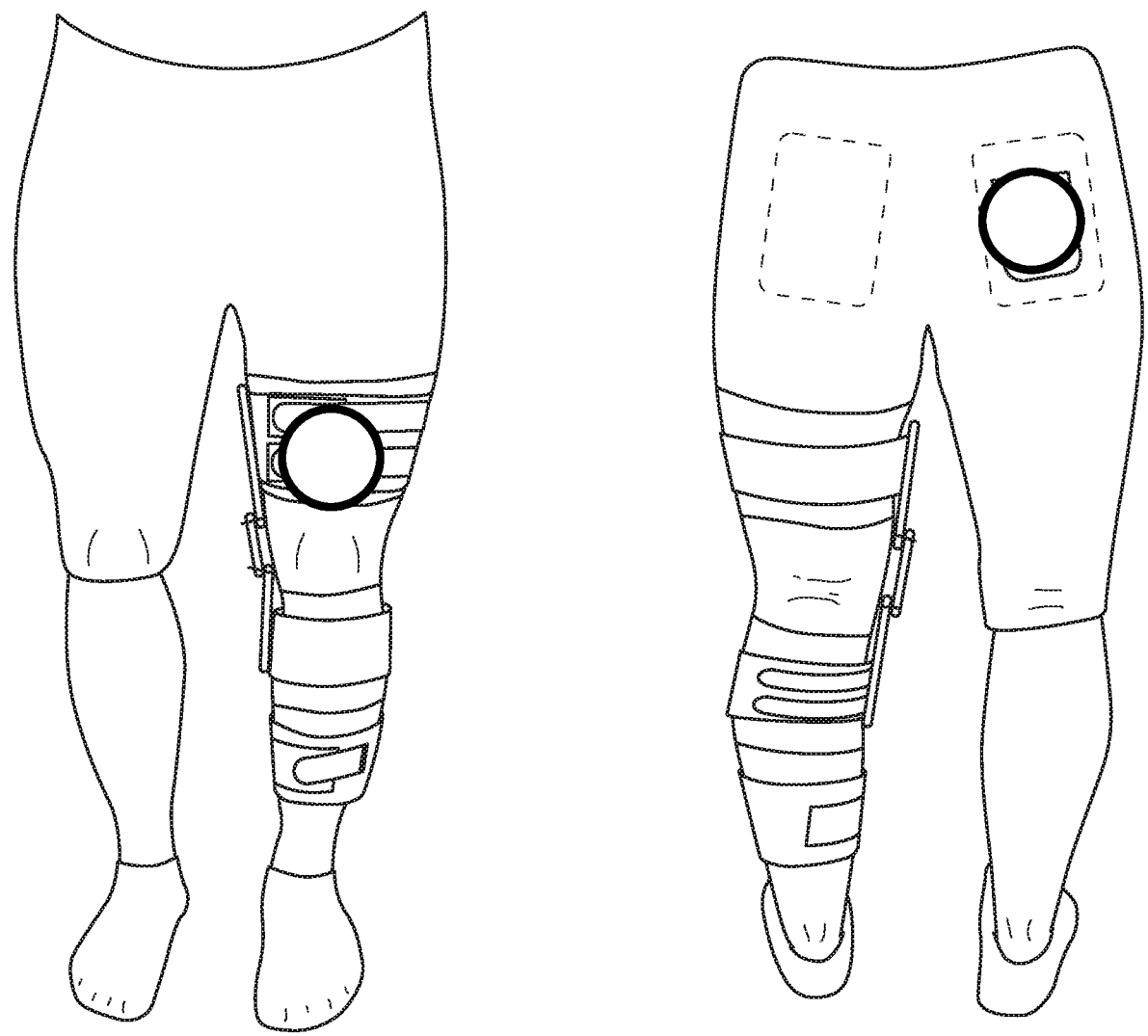
FIG. 16 is a schematic view of a sleeve of the invention with pockets for neuromodulation devices.

In some embodiments, the sleeve may include pockets into which neuromodulation devices, such as vibration devices, may be inserted in the sleeve to apply their therapeutic effect to the user. The locations for such pockets are shown in FIG. 16.

Figure 17:
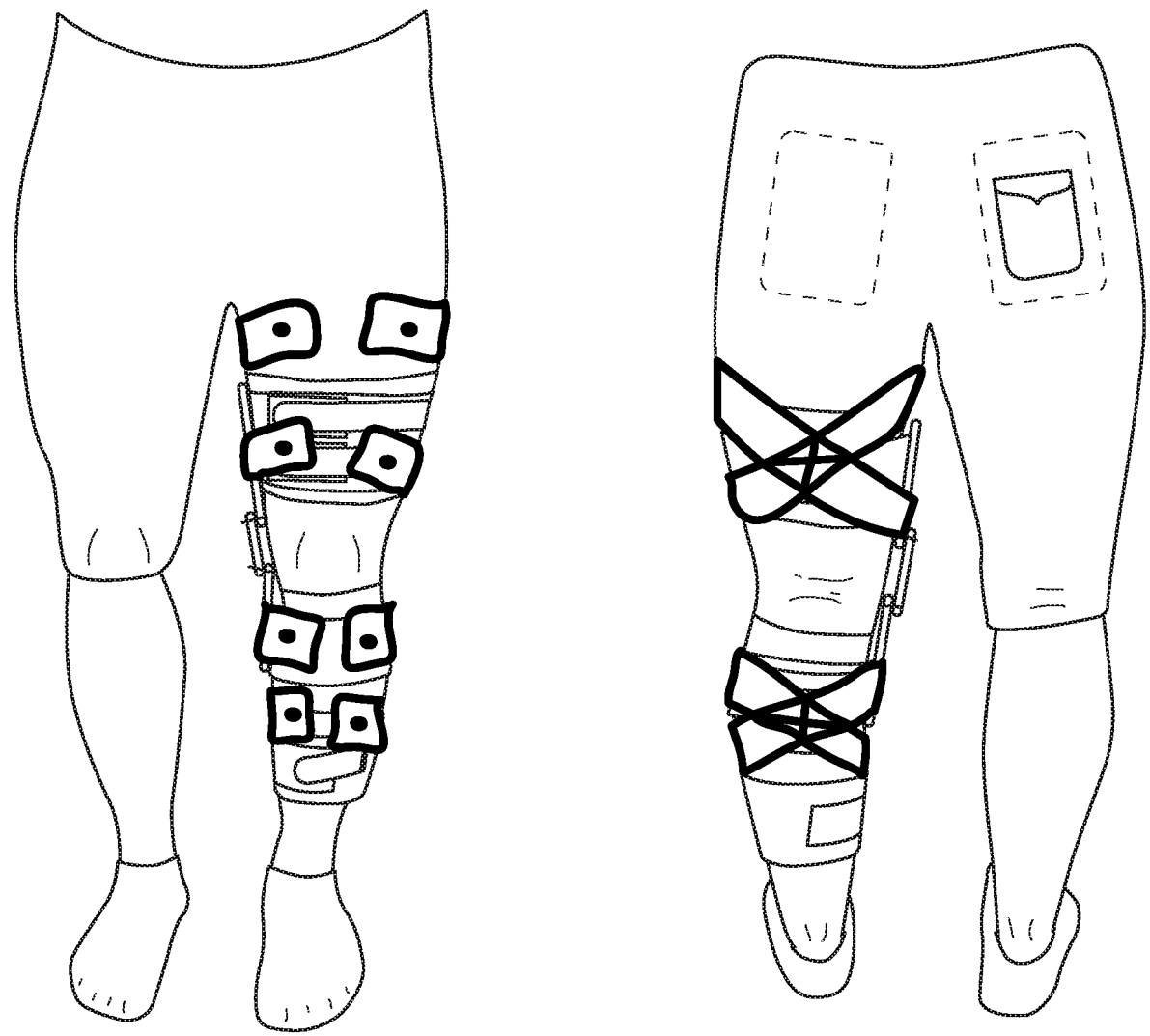
FIG. 17 is a schematic view of a specialized elastic strap having four ends employed in one embodiment of the invention.

FIG. 17 shows another embodiment of the invention where specialized elastic straps are employed. In this embodiment, each specialized strap has four ends joined at a center area. In some embodiments, the entire specialized strap may have between about 30% and about 60% elasticity, while in other embodiments, the center area of the strap may have less elasticity. For example, between about 0% and about 20%. Though the ends of the specialized strap are shown coupled with a front of the sleeve and mechanical joint brace, they may be coupled with the sides of the sleeve, and/or the backside of the mechanical joint brace in other embodiments. In any given embodiment, one to three ends of the specialized strap may be coupled with the sleeve, above or below the mechanical brace, while one to three ends of the specialized strap may be coupled with the mechanical joint brace, either on the lower or upper portion of the mechanical joint brace.

The invention has now been described in detail for the purposes of clarity and understanding. However, it will be appreciated that certain changes and modifications may be practiced within the scope of the appended claims.

What is claimed is:
1. A method for providing orthopedic support or therapy to a human body, wherein the method comprises:
  disposing a sleeve over a leg of a user such that:
    a first portion of the sleeve applies compressive pressure to the leg above a knee, wherein the first portion of the sleeve includes a first set of one or more pads at least partially encircling the leg above the knee; and
    a second portion of the sleeve applies compressive pressure to the leg below the knee, wherein the second portion of the sleeve includes a second set of one or more pads at least partially encircling the leg below the knee;
  disposing and tightening a mechanical joint brace over the sleeve, wherein:
    a first portion of the mechanical joint brace compresses the first set of one or more pads of the sleeve between the first portion of the mechanical joint brace and the leg above the knee;

a second portion of the mechanical joint brace compresses the second set of one or more pads of the sleeve between the second portion of the mechanical joint brace and the leg below the knee; and the mechanical joint brace has only one hinge which rotates about an axis passing through the knee;

coupling a first end of an elastic strap with some portion of the sleeve; and coupling a second end of the elastic strap with some portion of the mechanical joint brace.

2. The method for providing orthopedic support or therapy to a human body of claim 1, wherein:

the hinge of the mechanical joint brace is located on the inside of the knee, proximate to the other knee of the user.

3. The method for providing orthopedic support or therapy to a human body of claim 1, wherein:

the first end of the elastic strap is coupled with the sleeve proximate to a hip of the user;

the second end of the elastic strap is coupled with the second portion of the mechanical joint brace; and the elastic strap wraps around a longitudinal axis of the leg at least once.

4. The method for providing orthopedic support or therapy to a human body of claim 3, wherein:

the elastic strap wraps around a longitudinal axis of the leg at least twice.

5. The method for providing orthopedic support or therapy to a human body of claim 3, wherein:

proximate to the hip of the user comprises a side of the hip.

6. The method for providing orthopedic support or therapy to a human body of claim 3, wherein:

proximate to the hip of the user comprises a thigh below the hip.

7. The method for providing orthopedic support or therapy to a human body of claim 3, wherein:

proximate to the hip of the user comprises a waist above the hip.

8. The method for providing orthopedic support or therapy to a human body of claim 1, wherein:

the first end of the elastic strap is coupled with the sleeve proximate to a waist of the user;

the second end of the elastic strap is coupled with the second portion of the mechanical joint brace; and the elastic strap wraps around a longitudinal axis of the leg at least once.

9. The method for providing orthopedic support or therapy to a human body of claim 1, wherein:

the first end of the elastic strap is coupled with the sleeve proximate to a hip of the user; and the second end of the elastic strap is coupled with the first portion of the mechanical joint brace at an inside of a thigh of the leg.

10. The method for providing orthopedic support or therapy to a human body of claim 1, wherein:

the sleeve comprises:
  a first padded portion at an inner portion of the leg; and
  a second padded portion at an outer portion of the leg extending upward to a hip; and at least one of the first padded portion of the second padded portion is compressed between the elastic strap and the leg.

11. The method for providing orthopedic support or therapy to a human body of claim 1, wherein:

the first end of the elastic strap is coupled with the sleeve above the knee;

the second end of the elastic strap is coupled with the first portion of the mechanical joint brace; and the elastic strap wraps around a longitudinal axis of the leg at least once.

12. The method for providing orthopedic support or therapy to a human body of claim 1, wherein:

the first end of the elastic strap is coupled with the sleeve below the knee;

the second end of the elastic strap is coupled with the second portion of the mechanical joint brace; and the elastic strap wraps around a longitudinal axis of the leg at least once.

13. The method for providing orthopedic support or therapy to a human body of claim 1, wherein:

the elastic strap comprises a first elastic strap; and the method further comprises:
  coupling a second elastic strap at a first end with at least some portion of the mechanical joint brace or the sleeve; and
  coupling the second elastic strap at a second end with at least some portion of the mechanical joint brace or the sleeve.

14. The method for providing orthopedic support or therapy to a human body of claim 13, wherein:

the second elastic strap is less elastic than the first elastic strap; and the second elastic strap wraps substantially horizontally around a portion of the user.

15. The method for providing orthopedic support or therapy to a human body of claim 1, wherein:

the sleeve comprises a pocket; and the method further comprises disposing a vibration device within the pocket.

16. The method for providing orthopedic support or therapy to a human body of claim 15, wherein:

the pocket is located at a buttock or thigh of the user proximate to the knee.

17. The method for providing orthopedic support or therapy to a human body of claim 1, wherein:

the elastic strap comprises a specialized strap having four ends; and the method further comprises:
  coupling a third end of the elastic strap with some portion of the sleeve; and
  coupling a fourth end of the elastic strap with some portion of the mechanical joint brace.

18. A method for providing orthopedic support or therapy to a human body, wherein the method comprises:

disposing a sleeve over a leg of a user such that:
  a first portion of the sleeve applies compressive pressure to the leg above a knee, wherein the first portion of the sleeve includes a first set of one or more pads at least partially encircling the leg above the knee; and
  a second portion of the sleeve applies compressive pressure to the leg below the knee, wherein the second portion of the sleeve includes a second set of one or more pads at least partially encircling the leg below the knee;

disposing and tightening a mechanical joint brace over the sleeve, wherein:
  a first portion of the mechanical joint brace compresses the first set of one or more pads of the sleeve between the first portion of the mechanical joint brace and the leg above the knee;
  a second portion of the mechanical joint brace compresses the second set of one or more pads of the sleeve between the second portion of the mechanical joint brace and the leg below the knee; and the mechanical joint brace has only one hinge which rotates about an axis passing through the knee; and coupling a first end of an elastic strap with some portion of the mechanical joint brace, wherein a second end of the elastic strap is fixedly coupled with some portion of the sleeve.

19. A method for providing orthopedic support or therapy to a human body, wherein the method comprises:

disposing a sleeve over a leg of a user such that:

a first portion of the sleeve applies compressive pressure to the leg above a knee, wherein the first portion of the sleeve includes a first set of one or more pads at least partially encircling the leg above the knee; and a second portion of the sleeve applies compressive pressure to the leg below the knee, wherein the second portion of the sleeve includes a second set of one or more pads at least partially encircling the leg below the knee;

disposing and tightening a mechanical joint brace over the sleeve, wherein:

a first portion of the mechanical joint brace compresses the first set of one or more pads of the sleeve between the first portion of the mechanical joint brace and the leg above the knee;

a second portion of the mechanical joint brace compresses the second set of one or more pads of the sleeve between the second portion of the mechanical joint brace and the leg below the knee; and the mechanical joint brace has only one hinge which rotates about an axis passing through the knee; and coupling a first end of an elastic strap with some portion of the sleeve, wherein a second end of the elastic strap is fixedly coupled with some portion of the mechanical joint brace.

* * * * *